(12) United States Patent
Chronister et al.

(10) Patent No.: US 7,955,079 B2
(45) Date of Patent: Jun. 7, 2011

(54) DENTAL PROPHYLAXIS ANGLE AND HANDPIECE ASSEMBLY

(75) Inventors: Benjamin Chronister, York, PA (US); Jeremy Kile, Wrightsville, PA (US); Peter Werner, Columbia, PA (US); Bret Beane, Palatine, IL (US); Donald Heil, Lake Villa, IL (US); James Sherman, York, PA (US); Robert Whitcomb, Carlisle, PA (US)

(73) Assignee: Dentsply International, Inc., York, PA (US)

( * ) Notice: Subject to any disclaimer, the term of this patent is extended or adjusted under 35 U.S.C. 154(b) by 485 days.

(21) Appl. No.: 12/004,145

(22) Filed: Dec. 20, 2007

(65) Prior Publication Data

US 2009/0162811 A1   Jun. 25, 2009

(51) Int. Cl.
A61C 3/06 (2006.01)

(52) U.S. Cl. .................................. 433/125; 433/126

(58) Field of Classification Search .......... 433/125–126, 433/103, 114, 116, 118; 464/182; 15/167.1, 15/22.1
See application file for complete search history.

(56) References Cited

U.S. PATENT DOCUMENTS

| 3,407,502 | A | 10/1968 | Richmond |
|---|---|---|---|
| 3,478,433 | A | 11/1969 | Richmond |
| 3,691,636 | A | 9/1972 | Deuschle |
| 3,727,313 | A | 4/1973 | Graham |
| 3,740,853 | A | 6/1973 | Brahler |
| 3,835,858 | A * | 9/1974 | Hagen .......................... 606/180 |
| 3,939,599 | A * | 2/1976 | Henry et al. ..................... 433/99 |
| 4,182,041 | A | 1/1980 | Girard |
| 4,255,143 | A | 3/1981 | Schuss et al. |
| 4,266,933 | A | 5/1981 | Warden et al. |
| 4,365,956 | A | 12/1982 | Bailey |
| 4,486,175 | A | 12/1984 | Fisher et al. |
| 4,604,058 | A | 8/1986 | Fisher et al. |
| 5,020,994 | A * | 6/1991 | Huang ........................... 433/126 |
| 5,028,233 | A | 7/1991 | Witherby |
| 5,040,978 | A | 8/1991 | Falcon et al. |
| 5,083,922 | A | 1/1992 | Yale |
| 5,120,220 | A | 6/1992 | Butler |
| 5,131,846 | A | 7/1992 | Hall |
| 5,139,422 | A | 8/1992 | Straihammer et al. |
| 5,156,547 | A | 10/1992 | Bailey |
| 5,209,658 | A | 5/1993 | Brahler |
| 5,224,859 | A | 7/1993 | Kraenzle |
| 5,328,369 | A | 7/1994 | Bailey |
| 5,340,310 | A | 8/1994 | Bifulk |

(Continued)

FOREIGN PATENT DOCUMENTS

WO   WO 2006/017554   2/2006

*Primary Examiner* — Cris L Rodriguez
*Assistant Examiner* — Edward Moran
(74) *Attorney, Agent, or Firm* — Douglas J. Hura; Leana Levin; David A Zdurne

(57) ABSTRACT

A dental prophylaxis angle and handpiece assembly for cleaning and polishing teeth is provided. The dental prophylaxis angle is removably attached to the dental handpiece by an interlocking mechanism that includes extension locking tabs, a locking annular member, and an interlocking drive member in the handpiece. The prophy angle is securely snap-fitted onto the handpiece and locked in place so that it has minimal lateral movement. After the prophy angle has been used to treat a patient, it can be removed easily from the handpiece and disposed thereof.

28 Claims, 10 Drawing Sheets

U.S. PATENT DOCUMENTS

| | | | |
|---|---|---|---|
| 5,348,473 | A | 9/1994 | Kivlighan, Jr. |
| 5,352,119 | A | 10/1994 | Sakurai |
| 5,374,189 | A | 12/1994 | Mendoza |
| 5,380,202 | A | 1/1995 | Brahler |
| 5,382,162 | A | 1/1995 | Sharp |
| 5,405,265 | A | 4/1995 | Mendoza |
| 5,423,679 | A | 6/1995 | Bailey |
| RE34,997 | E | 7/1995 | Kraenzle |
| 5,433,605 | A | 7/1995 | Strobl, Jr. |
| 5,482,461 | A | 1/1996 | Yale |
| 5,484,284 | A | 1/1996 | Bailey |
| 5,496,218 | A | 3/1996 | Brahler |
| D368,523 | S | 4/1996 | Mendoza |
| D368,964 | S | 4/1996 | Mendoza |
| 5,503,555 | A | 4/1996 | Bailey |
| 5,507,644 | A | 4/1996 | Kivlighan, Jr. |
| D371,199 | S | 6/1996 | Mendoza |
| 5,529,495 | A | 6/1996 | Edwards |
| 5,531,599 | A | 7/1996 | Bailey |
| 5,554,896 | A | 9/1996 | Hogan |
| 5,571,012 | A | 11/1996 | Witherby et al. |
| D376,422 | S | 12/1996 | Bailey |
| 5,584,690 | A | 12/1996 | Maassarani |
| 5,642,995 | A | 7/1997 | Bailey |
| 5,645,426 | A | 7/1997 | Grim et al. |
| 5,655,906 | A | 8/1997 | Coss et al. |
| 5,667,383 | A | 9/1997 | Mendoza et al. |
| 5,683,247 | A | 11/1997 | Bailey |
| 5,690,488 | A | 11/1997 | Spinello |
| 5,692,901 | A | 12/1997 | Roth et al. |
| 5,730,595 | A | 3/1998 | Bailey |
| 5,749,728 | A | 5/1998 | Bailey |
| 5,775,901 | A | 7/1998 | Riso |
| 5,776,155 | A | 7/1998 | Beaupre et al. |
| 5,803,510 | A | 9/1998 | Dorsey, III |
| 5,824,289 | A | 10/1998 | Stoltz |
| 5,871,353 | A | 2/1999 | Pierce et al. |
| 5,876,203 | A | 3/1999 | Bailey |
| 5,902,107 | A | 5/1999 | Lowell |
| 5,911,577 | A | 6/1999 | Henrikson |
| 5,915,965 | A | 6/1999 | Ohlsson et al. |
| D413,384 | S | 8/1999 | Hanley et al. |
| D413,385 | S | 8/1999 | Hanley et al. |
| 5,964,590 | A | 10/1999 | Loddeke et al. |
| 6,012,922 | A * | 1/2000 | Novak .......................... 433/126 |
| 6,053,732 | A | 4/2000 | Sale |
| D427,311 | S | 6/2000 | Henrikson |
| 6,083,000 | A | 7/2000 | Charlton |
| 6,086,369 | A | 7/2000 | Sharp et al. |
| 6,089,866 | A | 7/2000 | Brahler |
| 6,099,309 | A | 8/2000 | Caidarelli |
| 6,146,140 | A | 11/2000 | Bailey |
| 6,168,433 | B1 | 1/2001 | Hamlin |
| 6,203,322 | B1 | 3/2001 | Kraenzle |
| 6,227,853 | B1 | 5/2001 | Hansen et al. |
| 6,247,931 | B1 | 6/2001 | Postal et al. |
| 6,257,886 | B1 | 7/2001 | Warner |
| 6,382,971 | B1 | 5/2002 | Randolph |
| 6,406,470 | B1 | 6/2002 | Kierce |
| 6,409,507 | B1 | 6/2002 | Postal et al. |
| 6,527,552 | B2 | 3/2003 | Loddeke et al. |
| 6,632,090 | B1 | 10/2003 | Randolph |
| 6,655,015 | B2 | 12/2003 | Kraenzle |
| 6,716,028 | B2 | 4/2004 | Rahman et al. |
| 6,811,399 | B2 | 11/2004 | Rahman et al. |
| 6,875,017 | B1 | 4/2005 | Tarr |
| 7,011,520 | B2 | 3/2006 | Rahman et al. |
| 7,047,706 | B2 | 5/2006 | Kraenzle |
| 7,070,412 | B2 | 7/2006 | Stadeker |
| 7,101,182 | B2 | 9/2006 | Garrison et al. |
| 7,104,794 | B2 | 9/2006 | Levy |
| 7,104,796 | B1 | 9/2006 | Chia et al. |
| 7,160,108 | B2 | 1/2007 | Jaffe |
| 7,217,128 | B2 | 5/2007 | Atkin et al. |
| 2002/0139091 | A1 | 10/2002 | Kraenzle |
| 2002/0192618 | A1 | 12/2002 | Loddeke et al. |
| 2005/0032022 | A1 | 2/2005 | Jaffe |
| 2005/0257372 | A1 | 11/2005 | Kraenzle |
| 2006/0024642 | A1 | 2/2006 | Stadeker |
| 2006/0046227 | A1 | 3/2006 | Shen et al. |
| 2006/0185322 | A1 | 8/2006 | Kraenzle |
| 2006/0204923 | A1 | 9/2006 | Stadeker |
| 2007/0026361 | A1 | 2/2007 | Carron |

* cited by examiner

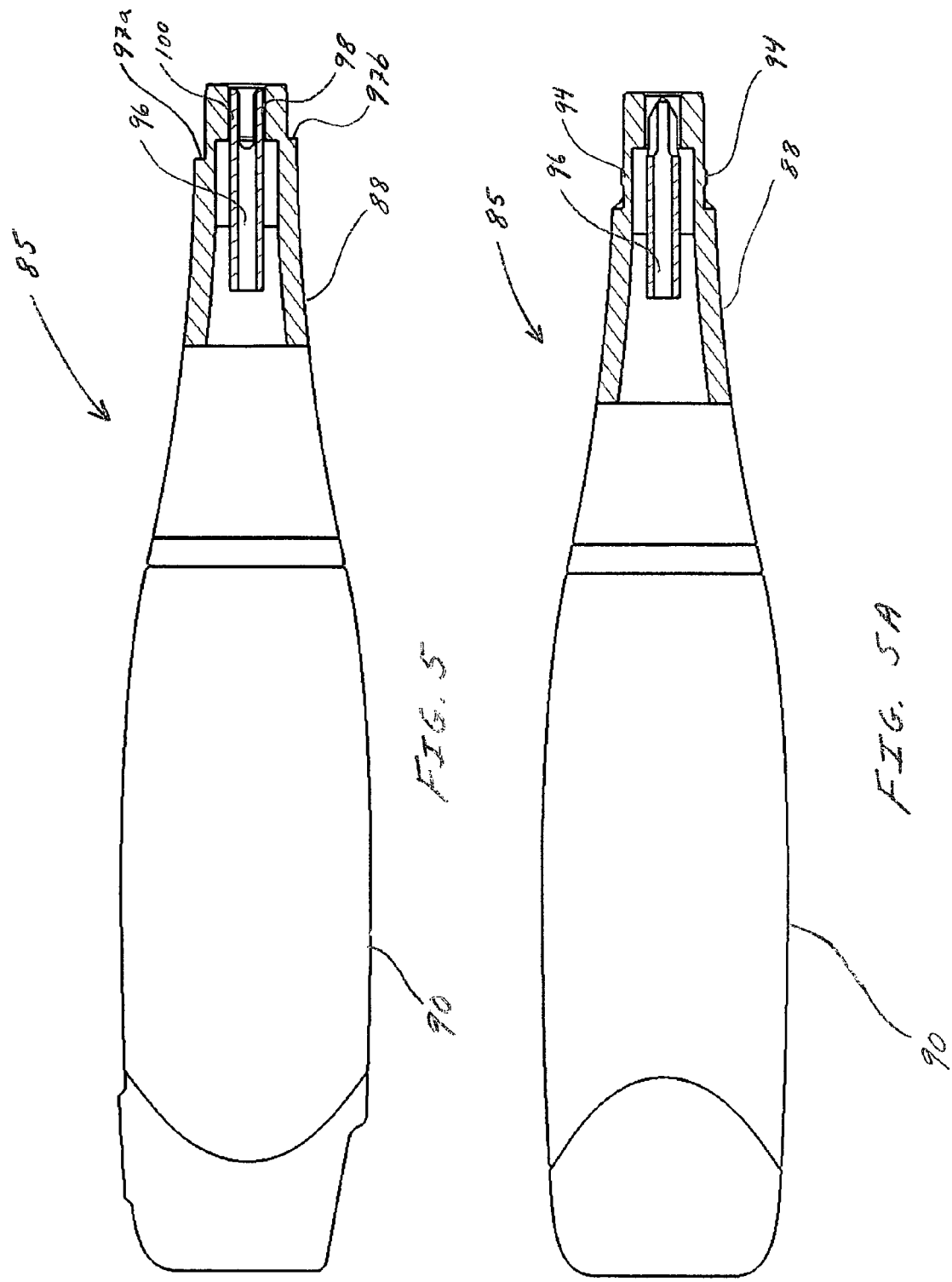

DENTAL PROPHYLAXIS ANGLE AND HANDPIECE ASSEMBLY

BACKGROUND OF THE INVENTION

1. Field of the Invention

The present invention relates generally to dental instruments used for cleaning and polishing teeth. More particularly, the invention relates to a dental prophylaxis angle and handpiece assembly. The dental prophylaxis angle is removably attached to the dental handpiece by a new interlocking mechanism.

2. Brief Description of the Related Art

Today, dental professionals use dental instruments commonly known as dental prophylaxis (prophy) angles for cleaning and polishing teeth. Referring to FIG. 1, traditional prophy angles (10) include a one-piece or multi-piece tubular housing (12) having sleeve (14), neck (16), and head (18) portions. Normally, the head portion (18) extends at an angle of ninety (90) degrees with respect to the neck portion (16). However, in some cases, contra-prophy angles having a head portion that extends at an angle of greater than 90 degrees are used. Dental professionals use the contra-prophy angles for cleaning hard-to-reach tooth surfaces. In both types of prophy angles, the tubular housing contains a relatively long drive shaft (20) having a driving gear (22) at its forward-facing end. The driving gear (22) of the drive shaft interacts with a driven gear (24) located in the head (18) of the prophy angle. A boss (25), which is located on top of the driven gear, is adapted for receiving a prophy cup or other dental tool. The driven gear (24) is integrally connected to a relatively short shaft (26).

The prophy angle (10) is attached to a dental handpiece (30) by inserting the drive shaft (20) into a chuck system (32) such as a collet or other retaining means in the handpiece, for example, ISO 3964 locking system. In addition, the sleeve portion (14) of the prophy angle contains a slot (15) which is adapted for receiving a standard positioning pin or finger (not shown) on the handpiece. The extended slot (15) permits the free end of the prophy angle to expand. The chuck jaws (32) hold the shaft (20) in place and operatively couples the shaft to an electrical or air-driven motor inside of the handpiece. The chuck jaws (32) rotate on anti-friction ball bearings (34) in the handpiece. When an operator powers on the handpiece, the connected drive shaft of the prophy angle rotates and the driving gear (22) intermeshes with the driven gear (24). This causes the prophy angle to rotate along with the attached prophy cup.

The prophy cup, which is filled with prophy paste, is pressed against the tooth surfaces to clean and polish the teeth. Different prophy pastes can be used depending upon the dental health of the patient and amount of dental plaque and calculus that needs to be removed. For example, NUPRO® prophylaxis paste, available from Dentsply International (York, Pa.) can be used as the prophy paste, and this paste is available in different textures (fine, medium, and coarse) depending upon the size of the abrasive particles used in the paste. Fluoride-containing and fluoride-free prophy pastes are available. A professional cleaning with prophy paste helps prevent dental caries caused by bacteria in dental plaque. Bacteria produce acids that eat into the tooth eventually causing cavities to form therein. When the teeth are cleaned and polished by a dental professional, the dental plaque can be effectively removed from the tooth surfaces of the patient. In addition, calculus build-up and extrinsic stains caused by beverages and food such as, for example, coffee, tea, or soda, also can be effectively removed. The prophy angles are normally made from an inexpensive, flexible plastic and the prophy cup is made from a rubbery material. The dental professional disposes the prophy angles and cups after one-time use on a patient.

There are numerous dental prophy angles and prophy pastes systems known in the dental field including, for example, Upgrade® disposable prophy angles (Sultan Dental Products); All Pro® disposable prophy angles (Young Dental Manufacturing Colo.); and NUPRO Revolv® disposable prophy angles (Dentsply International). Different handpiece connection systems for attaching the prophy angles are described in the patent literature.

For example, Kivlighan, U.S. Pat. No. 5,348,473 discloses a medical tool such as a dental prophylaxis angle. The housing is made of two plastic halves which snap-fit together. The right-hand housing portion includes ridges that project into the cavities of the left-hand housing portion. The housing portions are connected by pushing them towards each other so that the ridges on the first housing portion project into the cavities of the opposing housing portion. The locking ridges are forced into the locking cavities to maintain the two portions in their locked position.

Bailey, U.S. Pat. No. 5,531,599 discloses plastic, easy-to-assemble dental prophylaxis contra-angles, wherein the head of the prophy angle is angled at an angle greater than 90 degrees with respect to the handpiece. An elongated slot in the body of the prophy angle permits the body to be force-fit onto a standard dental handpiece. The body of the prophy angle can be slipped over the nose of a handpiece, such as a Doriot type handpiece having a collet, which receives the drive shaft of the angle.

Bailey, U.S. Pat. No. 5,683,247 discloses a maintenance-free dental prophylaxis angle comprising a one-piece body including a sleeve and a head. The angle is designed to be used for an extended period of time, for example, one year without requiring any lubrication. The angle includes an internal lubricant circulating system. A slit is cut into the sleeve of the prophy angle and this creates two spring fingers which expand slightly when the angle is placed on a handpiece. This creates a size-on-size frictional fit with the nose of the handpiece and it to hold the prophy angle body independently of the handpiece chuck.

Kraenzle, U.S. Pat. No. 6,203,322 discloses a dental prophy angle having a forward end formation with a hinged closure that allows access to the gears and drive shaft inside of the angle. The closure is secured in a fixed position on the forward end formation by locking elements. The prophy angle includes a drive shaft that drives a rotor in the head of angle. The drive shaft is driven by a driving mechanism in a dental handpiece and the prophy angle is attached to the handpiece in a conventional fashion.

Conventional dental prophy angles and handpiece systems are generally effective; however, there is a need for an improved system. Traditional systems can have some drawbacks. For example, after prolonged use and excessive vibrational motion, some drive shafts of some prophy angles can shear off in the handpiece. The broken-off drive shaft can be difficult to remove from the handpiece and normally it must be returned to the factory for repair. Another problem with some conventional prophy angle and handpiece systems is that the prophy angle shows poor stability when it is mounted on the handpiece. Some prophy angles tend to wobble and rock. The prophy angles have excessive lateral movement. This can cause significant problems when the prophy angle/handpiece assembly is being used during a cleaning procedure. A dental professional may feel uncomfortable using such an unstable prophy angle/handpiece assembly, and it may cause added anxiety for the user and patient being treated.

Thus, there is a need in the dental industry for a prophy angle and handpiece assembly which is more stable and feels more comfortable. The assembly should have a good ergonomic design and be durable and lightweight. It is important that the prophy angle and handpiece assembly have good dimensional stability so that the prophy angle does not wobble and rock freely while it is being used. The prophy angle should be locked securely onto the handpiece. At the same time, a dental professional should be able to remove the prophy angle easily in order to substitute a new prophy angle in place thereof as needed. The present invention provides such a prophy angle and handpiece assembly having these objects, features, and advantages as well as others.

SUMMARY OF THE INVENTION

The present invention is directed to a dental handpiece and prophy angle assembly used for cleaning and polishing teeth. The prophy angle is removably attached to the handpiece. The invention also encompasses the prophy angle by and in itself. The prophy angle comprises an elongated tubular body with proximal and distal end portions. The proximal end portion includes a hollow head member. The head member may include a hinged closure, which opens, so that the chamber of the head member and central bore of the tubular body are accessible. The hinged closure can be secured to the prophy angle by locking detents on the head member that snap into slots in the hinged closure.

A first (driven) gear is mounted in the hollow head chamber. A prophylaxis cup containing prophy paste or a prophylaxis brush cup can be supported by the driven gear. The central bore of the prophy angle contains a drive shaft having a second (driving) gear on its forward-facing end for driving the driven gear. In one embodiment, the axis of the driven gear is angled at 90 degrees with respect to the axis of the driving gear. In other embodiments, the axis of the driven gear is angled at an angle in the range of about 90 to about 130 degrees, preferably 108 degrees. Preferably, the driven gear and driving gear each include beveled gear teeth that are staggered in relation to each other so that the respective gear teeth can intermesh together.

The rear-facing end of the drive shaft has a piloting tip for guiding the prophy angle onto the dental handpiece. The drive shaft also includes protruding self-aligning tabs that define a recessed locking surface adapted for receiving an interlocking drive member located in the handpiece. The distal end of the prophy angle is open-ended so that it can be mounted onto the handpiece. The distal end includes a first locking extension with first locking tab and a second locking extension with second locking tab. The external surface of the prophy angle may include a handle area having a textured external surface for providing a better grip and feel.

The dental handpiece includes a forward-facing tubular nose portion and a rear-facing handle portion. The nose portion includes a central aperture adapted for receiving the piloting tip of the drive shaft and a locking annular member for engaging the first and second locking tabs of the prophy angle. The nose position of the handpiece further contains an interlocking drive member having first and second self-aligning forward-facing extension prongs that define a locking slot. As the prophy angle and handpiece are assembled together, the extension prongs of the drive member in the handpiece slide into the recessed locking surface of the drive shaft in the prophy angle. The nose portion of the dental handpiece may include nesting cut-out portions and the locking extensions located on the distal end of the prophy angle mate with these complementary-shaped cut-out portions. In a similar manner, the distal end of the prophy angle may include locking recessions and the nose portion of the dental handpiece may include complementary-shaped nesting surfaces. The locking recessions of the prophy angle mate with the nesting surfaces of the dental handpiece when the assembly is in a locked position.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description in connection with the accompanying drawings in which:

FIG. 5 is a partial cross-sectional (through the extension prongs of the drive member) side perspective view of one embodiment of the handpiece of this invention;

FIG. 5A is a partial cross-sectional (through the locking slot between the extension prongs) side perspective view of one embodiment of the handpiece of this invention;

DETAILED DESCRIPTION OF THE PREFERRED EMBODIMENTS

Figure 1:
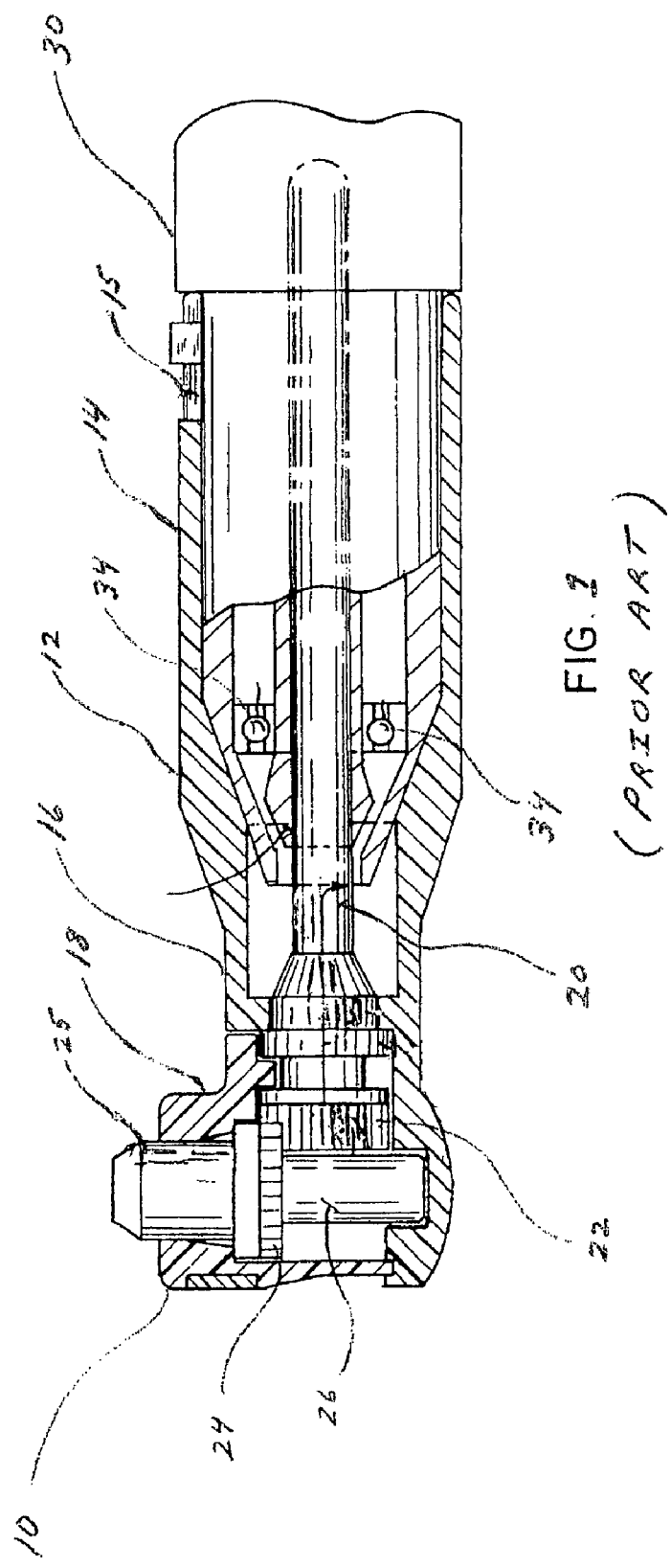
FIG. 1 is a side cross-sectional view of a prophy angle and handpiece assembly of the prior art.
Figure 2:
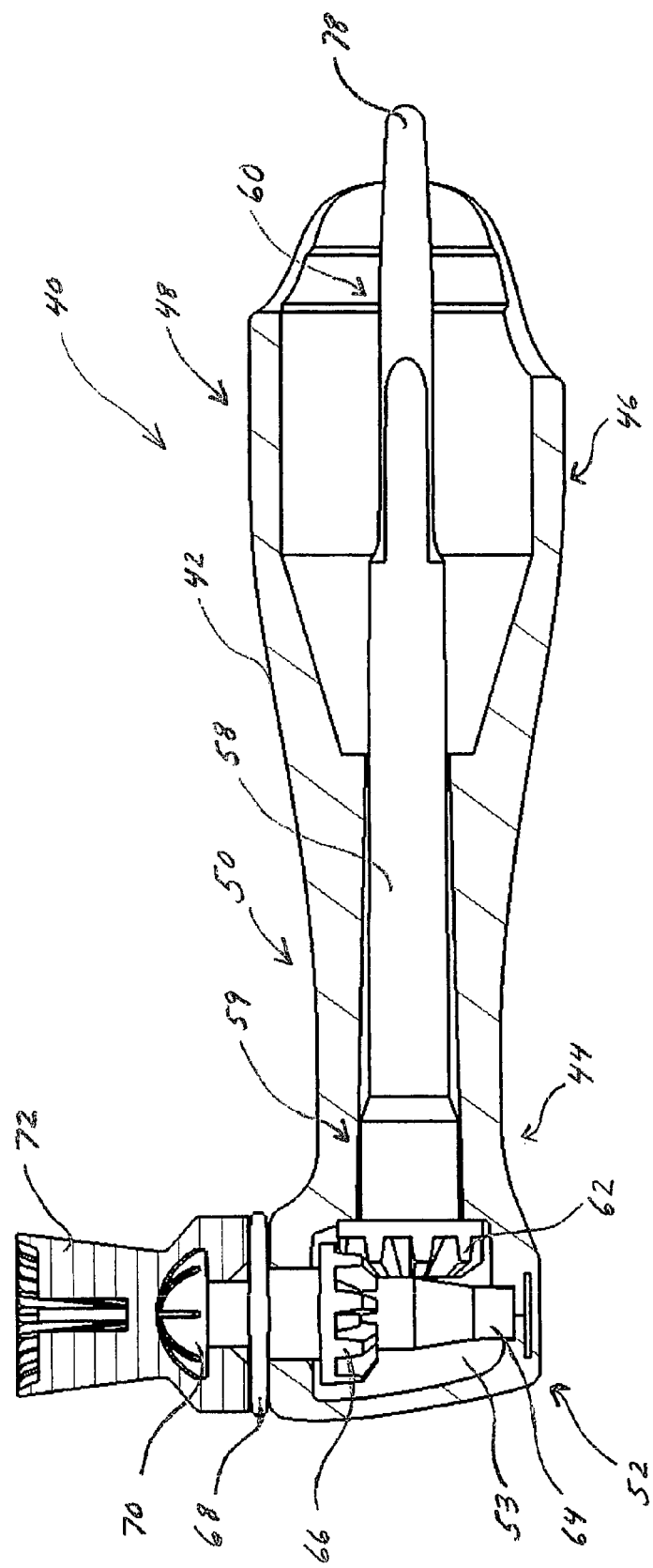
FIG. 2 is a side partial cross-sectional view of one embodiment of the prophy angle of this invention.

Referring to the drawings, the prophy angle of the instant invention is generally indicated at (40) in FIG. 2. As will be hereinafter more fully described, the prophy angle (40) generally comprises an elongated tubular body (42) with proximal (44) and distal (46) end portions. The tubular body (42) includes a handle or sleeve region (48), a neck region (50), and a head region (52) that defines a hollow chamber (53). The interior of the tubular body (42) defines a central bore extending from the proximal (44) to distal (46) end portions. The bore in the handle (48) has substantially the same diameter as the diameter of the dental handpiece (not shown) that will receive the prophy angle (40). The diameter of the bore tapers off so that the neck region (50) has a smaller diameter than the handle (48). The distal end (46) of the tubular body (42) includes a first locking extension (54) with a first locking tab (55) and an opposing second locking extension (56) with a second locking tab (57) (FIG. 6A). It should be understood that the tubular body (42) could contain more than two extension tabs. For example, the tubular body (42) could include four extension tabs in another version. The distal end (46) of the tubular body (42) is open-ended so that the prophy angle (40) can slide onto a dental handpiece as described further below.

The central bore of the prophy angle (40) further includes a drive shaft (58) having forward-facing (59) and rear-facing (60) end portions. The drive shaft (58) is positioned inside of the bore so that extends along the longitudinal axis of the bore and is generally co-axial thereto. The forward end (59) of the shaft (58) includes an integrally connected driving gear (62) that extends into the hollow head (53). The drive shaft (58) may be referred to as a "long gear." The hollow head (53) encloses a rotor (64) having a driven gear (66), which may be referred to as a "short gear." In FIG. 2, the axis of the driven gear (66) is angled at ninety (90) degrees with respect to the axis of the driving gear (62) for illustration purposes only. It should be understood that the axis of the driven gear (66) may be angled at greater than ninety (90) degrees with respect to the axis of the driving gear (62) if such a configuration is desired. For example, in other embodiments, the axis of the driven gear (66) may be disposed at an angle greater than ninety (90) degrees, preferably 108 degrees.

The rotor (64) mounted in the head chamber (53) further includes a flange (68) and button head (70) adapted for receiving a prophylaxis cup (72) or other dental element. Although the prophy angle (40) will be described herein as including a prophylaxis cup for cleaning and polishing the teeth, it should be understood that a brush or other dental element may be mounted on the prophy angle (40) if desired. In operation, the teeth of the short gear (66) engage the complementary teeth of the long gear (62) in the head chamber (53). The teeth are staggered in relation to each other so that the teeth along the short gear (66) will conform to the recesses located between the teeth of the long gear (62). As the driving gear (62) rotates about the axis of the drive shaft (58), the driving gear (62) intermeshes with the driven gear (66). The driving gear (62) transfers rotating motion to the driven gear (66). This causes the driven gear (66) and attached prophy cup (72) to rotate. The rotating prophy cup (72), which contains prophy paste, is applied to the tooth surfaces to clean and polish the teeth of the patient.

Figure 3:
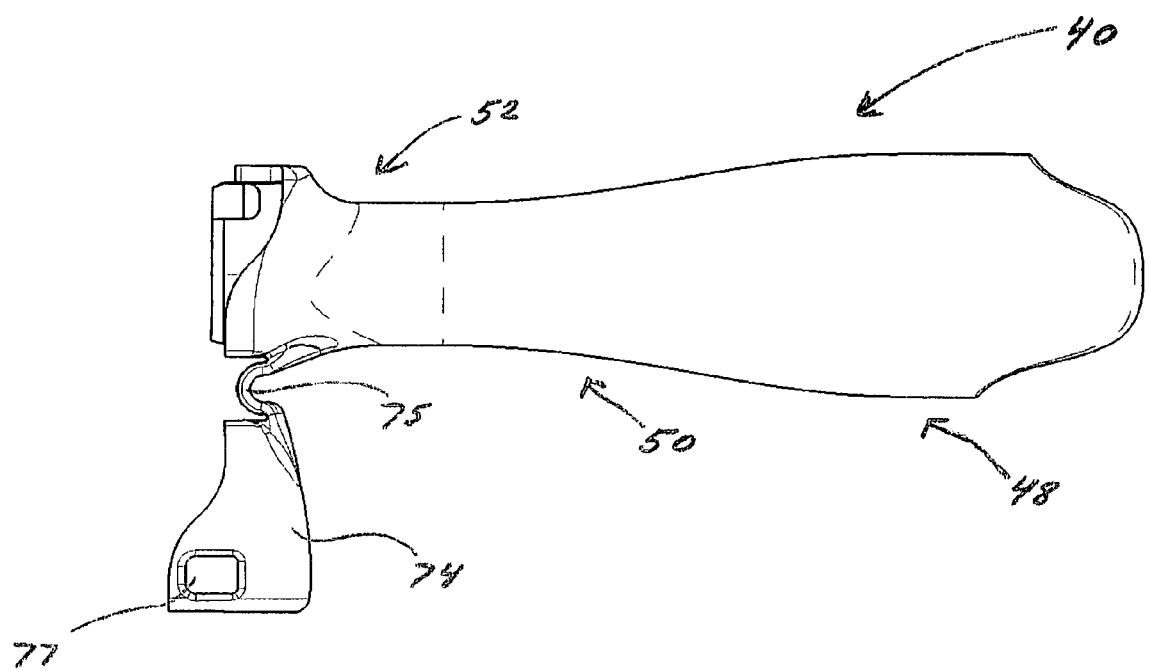
FIG. 3 is a side perspective view of one embodiment of the prophy angle of this invention.

As shown in FIG. 3, the head portion (52) of the prophy angle (40) may include a closing member (74) that pivots on a hinge (75). When the hinged closing member (74) is pulled open, the bore of the tubular body (42) and the head chamber (53) are accessible. When the prophy angle (40) is being used, the hinged closing member (74) remains in a closed position. The hinged closing member (74) may be secured to the external surface of the tubular body (42) by locking detents (76) located on the head portion (52) of the prophy angle that snap into slots (77) on the hinged closing member. In addition, the handle portion (48) may have a textured external surface (for example, dimples, recessed features, or the like) to provide the user with a better grip, control, and tactile feel.

Figure 4:
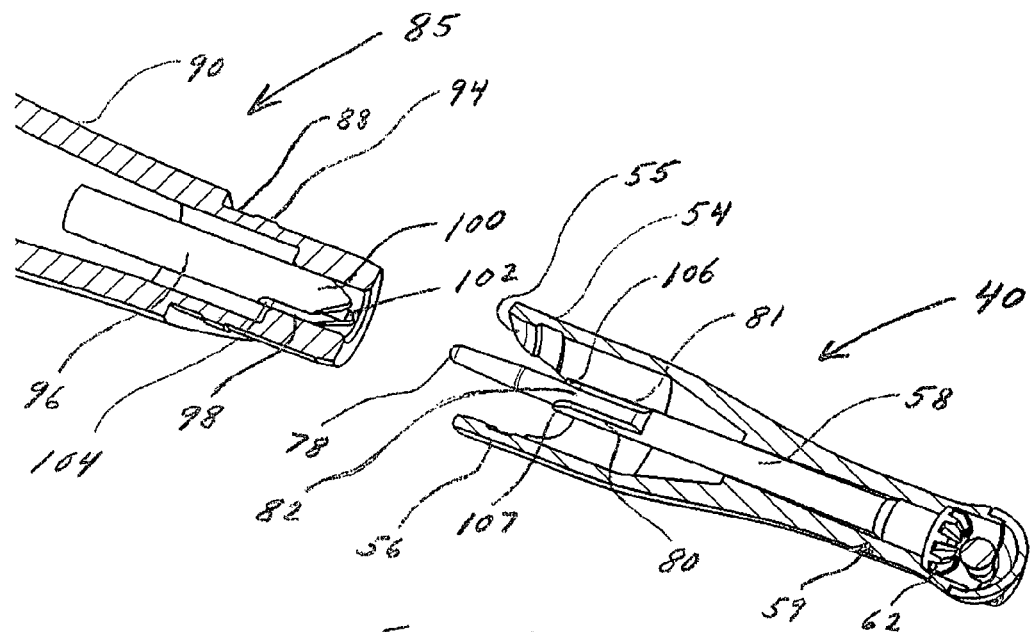
FIG. 4 is a partial cross-sectional exploded view of one embodiment of the assembly of this invention showing the drive shaft of the prophy angle and drive member of the handpiece.
Figure 4A:
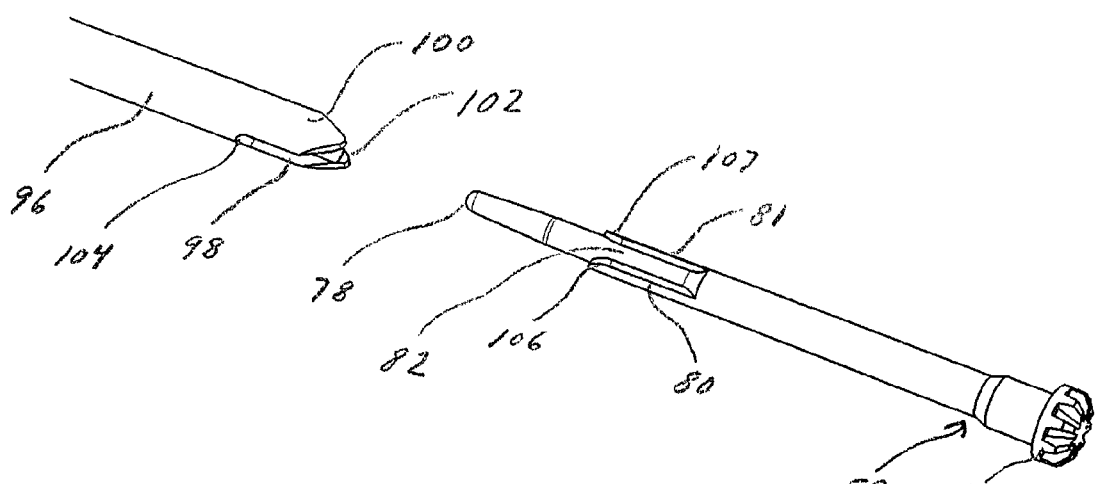
FIG. 4A is an exploded view of one embodiment of the assembly of this invention showing the drive shaft of the prophy angle and drive member of the handpiece.

Referring to FIG. 4, the rear-facing end (60) of the drive shaft (58) further includes first (80) and second (81) self-aligning tabs that form a recessed locking surface (82) located there between. The self-aligning tabs (80, 81) are perpendicular with respect to the longitudinal axis of the entire drive shaft (58). The recessed locking surface (82) of the drive shaft (58) is of sufficient length so that it is capable of receiving a drive member (96) located in the dental handpiece (85) as discussed further below.

Figure 6:
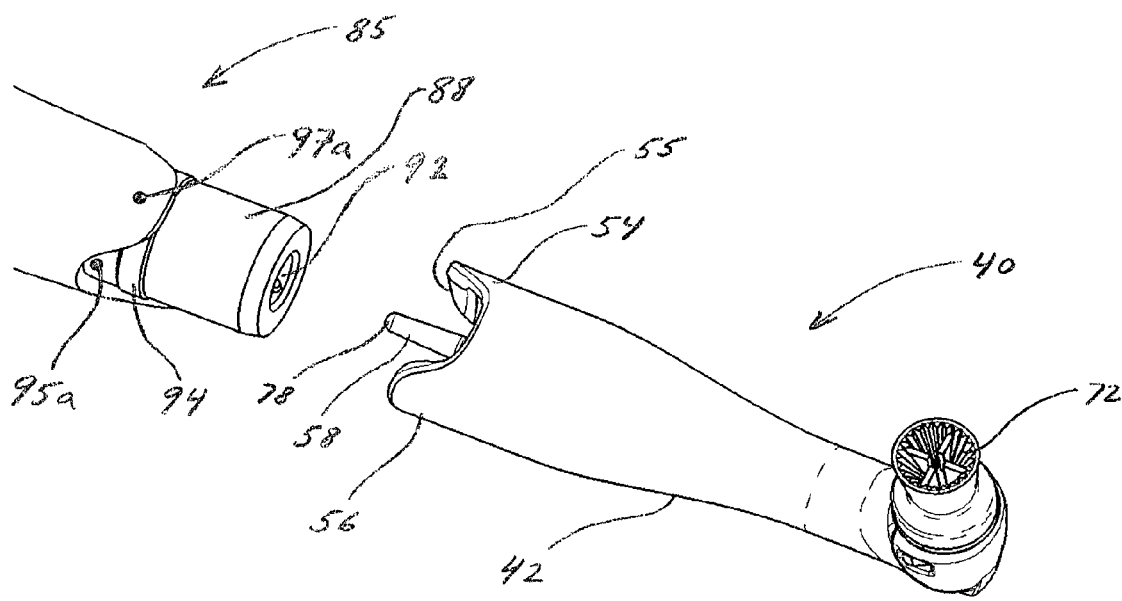
FIG. 6 is an exploded view of one embodiment of the prophy angle and handpiece of this invention.
Figure 6A:
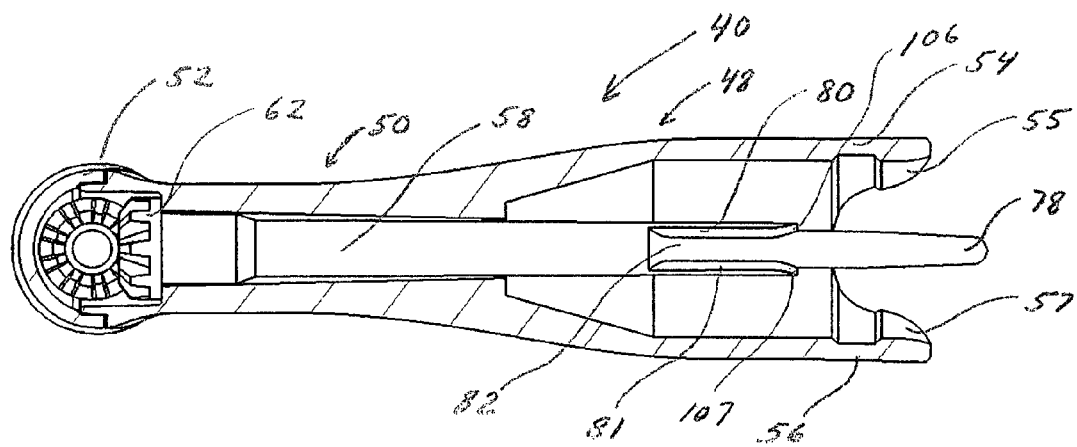
FIG. 6A is a rear partial cross-sectional view of one embodiment of the prophy angle of this invention.

As shown in FIGS. 6 and 6A, the drive shaft (58) is of sufficient length so that it extends beyond the rear-facing opening of the tubular body (42) and can be inserted into a dental handpiece (85). It is not necessary for the drive shaft (58) to extend beyond the open-ended distal portion (46) of the tubular body (42). In other embodiments, the drive shaft (58) may have a shorter length. The drive shaft (58) further includes a piloting tip (78) for guiding the prophy angle (40) onto the handpiece (85) and into the drive member (96). The first locking extension (54) with first locking tab (55) and second locking extension (56) with second locking tab (57) are used to lock the prophy angle (40) in place after it has been inserted onto the handpiece (85) as discussed further below.

In FIGS. 5 and 6, a dental handpiece (85), suitable for receiving the prophy angle (40), is shown. The handpiece (85) includes a forward-facing tubular nose portion (88) and a rear-facing handle portion (90). Preferably, the handpiece (85) is powered by batteries (not shown) located in a battery compartment in the handle portion (90). The nose portion (88) includes a central aperture (92) adapted for receiving the drive shaft (58) of the prophy angle (40). The nose portion (88) contains an interlocking drive member (96) having first (98) and second (100) self-aligning extension prongs for driving the drive shaft (58).

Figure 7:
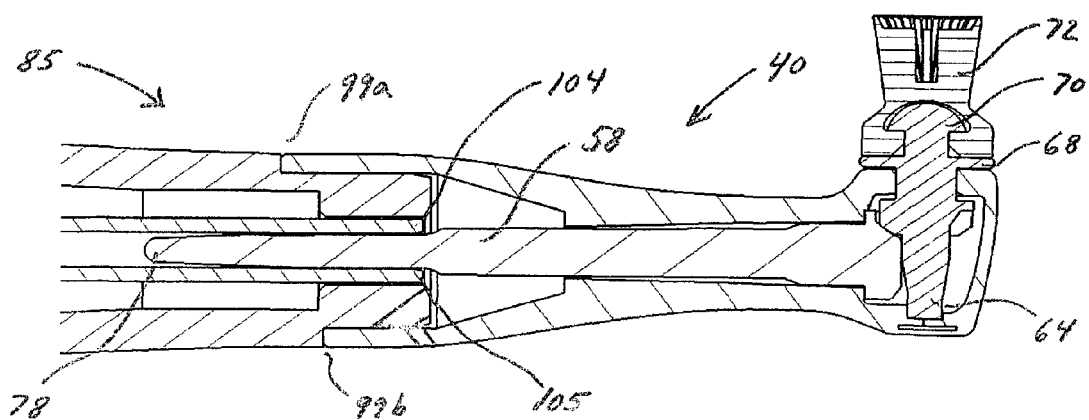
FIG. 7 is a side cross-sectional view (through the extension prongs of the drive member) of one embodiment of the assembly of this invention showing the prophy angle attached to the handpiece.

As further shown in FIG. 6, the nose portion (88) of the handpiece (85) includes a locking annular member (94) adapted for engaging the first and second locking tabs (55, 57) of the prophy angle (40). It is recognized that the locking annular member (94) may be protruding or recessed. The nose portion (88) also includes indented surface areas (95) on its external body. These indented areas or nesting cut-outs (95) are adapted for receiving the locking extensions (54, 56) of the prophy angle (40). The locking extensions (54, 56) of the prophy angle (40) mate with the complementary-shaped nesting cut-outs (95) of the handpiece (85). In a similar manner, the handpiece (85) includes a nesting surface (97) that mates with the complementary-shaped locking recessions (99) of the prophy angle (40) (FIG. 7).

Turning back to FIG. 4, the interlocking drive member (96) having first and second self-aligning extension prongs (98, 100) is shown being assembled onto the drive shaft (58). The prongs (98, 100) define an open locking slot (102) located there between so that the drive member (96) can slide onto the drive shaft (58). A conventional drive source (not shown) such as a motor can be used to drive the drive member (96); the drive source is located in the handpiece (85). The drive source is operatively coupled to the drive member (96), which drives the drive shaft (58).

Figure 8:
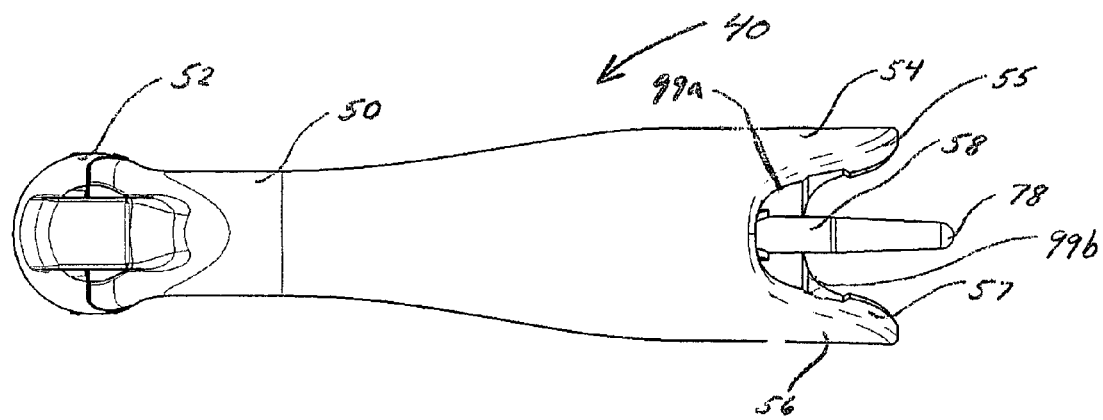
FIG. 8 is a rear perspective view of one embodiment of the prophy angle showing the offset locking recessions.
Figure 9:
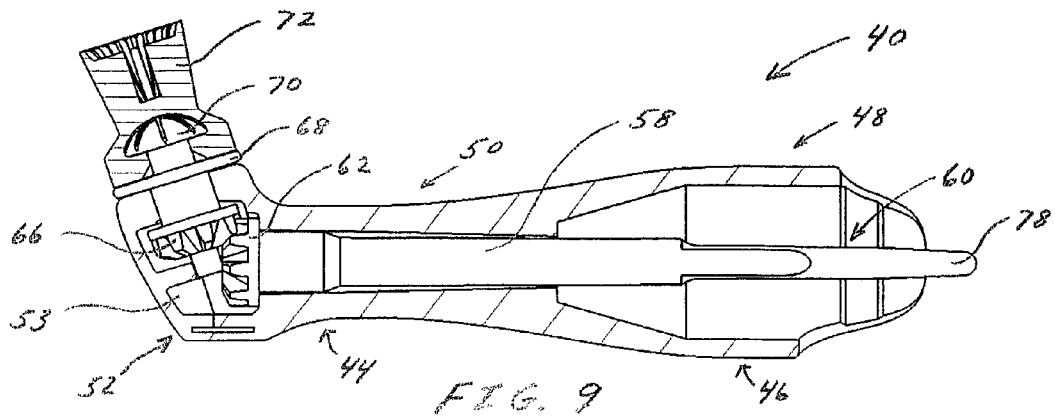
FIG. 9 is a side partial cross-sectional view of another embodiment of the prophy angle of this invention showing the axis of the driven gear angled at greater than ninety degrees with respect to the axis of the driving gear.
Figure 9A:
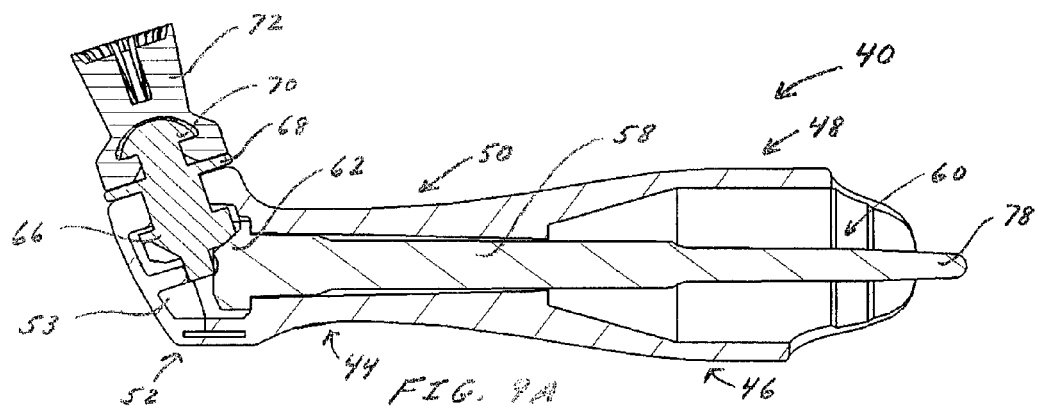
FIG. 9A is a side full cross-sectional view of the prophy angle shown in FIG. 9.
Figure 9B:
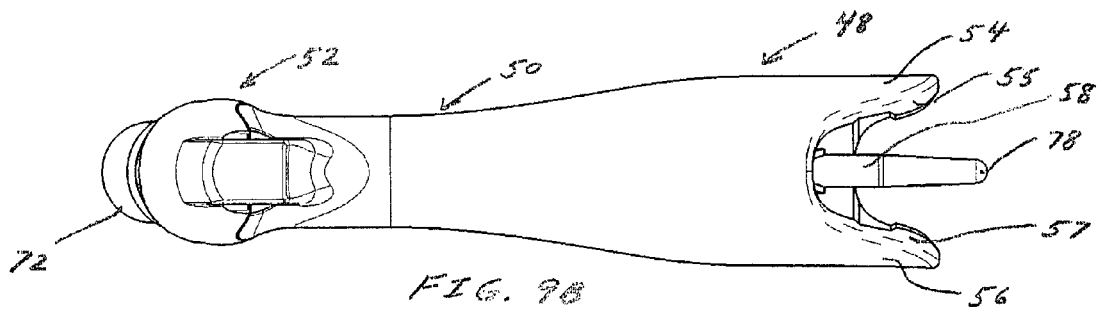
FIG. 9B is a rear perspective view of the prophy angle shown in FIG. 9.
Figure 9C:
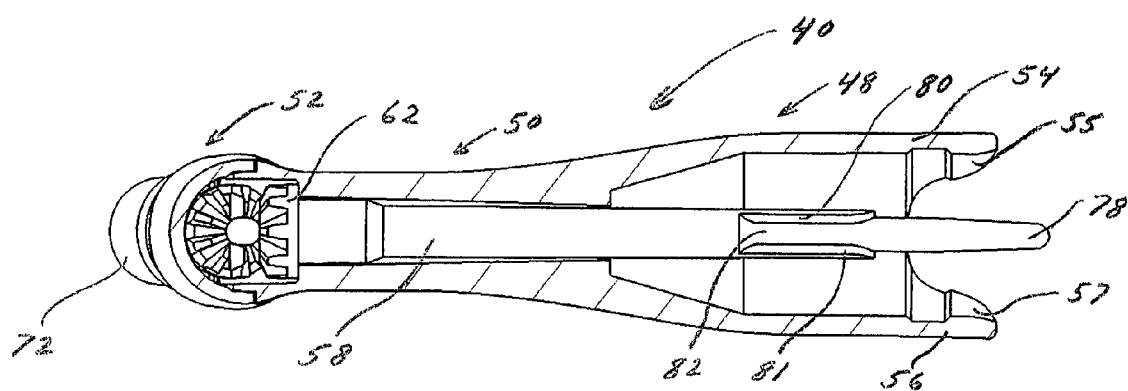
FIG. 9C is a rear partial cross-sectional view of the prophy angle shown in FIG. 9.
Figure 9D:
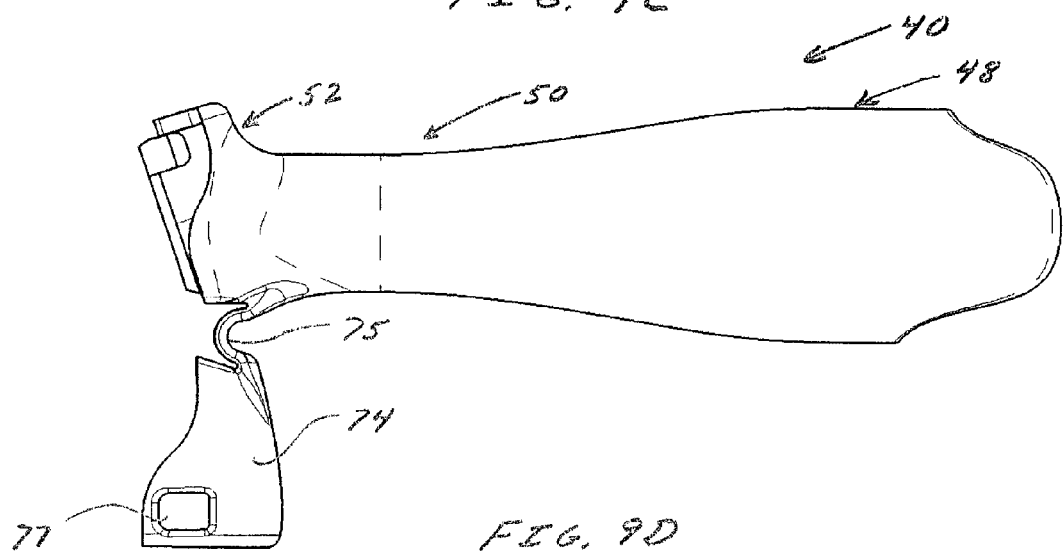
FIG. 9D is a side perspective view of the prophy angle body shown in FIG. 9.

In FIG. 6, the prophy angle (40) is shown being placed on the dental handpiece (85). Here, the piloting tip (78) of the drive shaft (58) is guided into the central aperture (92) of the nose portion (88) and the locking tabs (55, 57) catch and lock with the protruding inner annular member (94). Meanwhile, the locking extensions (54, 56) of the prophy angle (40) slide into the nesting cut-outs (95a, 95b) surrounding the nose portion (88) of the handpiece (85). The complementary-shaped nesting cut-outs (95a, 95b) on the surface of the handpiece (85) receive the locking extensions (54, 56). This creates a keying mechanism between the prophy angle (40) and handpiece (85). As shown in FIG. 8, the first locking recession (99a) of the prophy angle (40) may have different dimensions than the second locking recession (99b) so they are offset. These locking recessions (99a, 99b) mate with the complementary-shaped nesting surfaces (97a, 97b) of the handpiece (85), which are also offset. In a preferred embodiment the locking recessions (99a, 99b) are offset, but they can be configured in parallel in other versions of the prophy angle (40). For example, in an alternative version, the respective locking recessions (99a, 99b) on the prophy angle (40) have the same dimensions and are not offset. These locking recessions (99a, 99b) mate with the corresponding nesting surfaces (97) of the handpiece (85), which also are not offset.

Figure 7A:
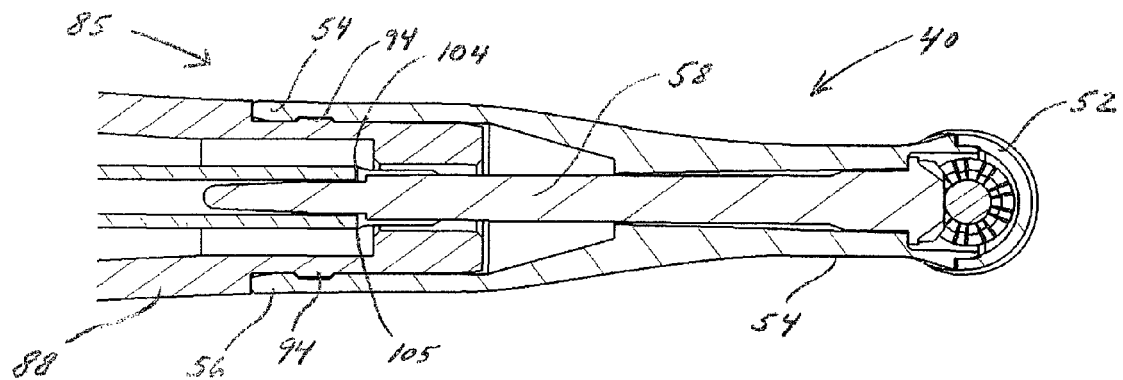
FIG. 7A is a rear cross-sectional view (through the locking slots between the extension prongs) of one embodiment of the assembly of this invention showing the prophy angle attached to the handpiece.

The above-described keying mechanism provides the prophy angle and handpiece assembly of this invention with improved stability. As the locking extensions (54, 56) slide into the nesting cut-outs (95a, 95b) of the handpiece (85), the drive member (96) inside of the handpiece (85) slides onto the recessed locking surface (82) of the drive shaft (58). The drive member (96) slides onto the locking surface (82) so that the notches (104, 105) of the extension prongs (98, 100) make contact with the shoulder abutments (106, 107) of the first and second self-aligning tabs (80, 81) of the drive shaft (58). In FIGS. 7 and 7A, the prophy angle (40) is shown locked in place on the dental handpiece (85). In the locked position, the locking tabs (55, 57) of the prophy angle (40) are locked with the inner annular member (94) of the handpiece (85).

Basically, a dental professional can load the prophy angle (40) by pushing the prophy angle (40) onto the dental handpiece (85) until he or she feels the resistance of the protruding internal locking annular member (94). The keying features of the prophy angle (40) and handpiece (85), as described above, ensure that the prophy angle (40) can only be inserted onto the handpiece (85) in one direction. The user should continue pushing the prophy angle (40) slightly further until feeling the "click" of the extension locking tabs (55, 57) snapping over the locking annular member (94). The force applied to the prophy angle (40) causes the locking tabs (55, 57) to deflect and snap over the annular member (94). The snapping of the locking tabs (55, 57) over the annular member (94) may be audible to the user. In this manner, the prophy angle (40) is securely snap-fitted onto the handpiece (85). Once the prophy angle (40) has been inserted onto the handpiece (85) and locked in place, it has minimal lateral and angular movement. The prophy angle (40) does not rotate or wobble or rock freely.

The prophy angle (40) and handpiece (85) members are self-aligning and this further helps control lateral and rotational motion of the prophy angle (40) after it has been inserted onto the handpiece (85). In addition, the nose portion (88) of the handpiece (85) is relatively long and this helps improve the stability of the assembly. The locked prophy angle and handpiece assembly has good ergonomics, is very stable, and feels comfortable to the user. The system of this invention provides other advantages. For example, if the drive shaft (58) of the prophy angle (40) accidentally breaks-off inside of the handpiece (85) so that one piece of the shaft (58) remains in the prophy angle (40) and the other piece remains in the handpiece (85), the broken piece inside of the handpiece can be removed easily. The user simply needs to invert the handpiece (85) and the broken piece will fall out. This is a significant advantage over conventional handpiece and prophy angle systems having drive shafts that break-off in the handpiece. In such systems, the user normally needs to return the handpiece to the manufacturer or distributor for repair service.

The above-described interlocking system prevents the prophy angle from disengaging while it is being used to clean and polish the teeth of a patient. At the same time, a dental professional can remove the old prophy angle easily when the assembly is not being used, dispose of it, and substitute a new prophy angle in place thereof to treat a new patient.

To remove the prophy angle (40) from the handpiece (85), the user pinches the prophy angle (40) slightly and pulls on it outwardly. The force applied to the prophy angle (40) causes the extension tabs (55, 57) to snap over the annular member (94). The prophy angle (40) is pulled in a linear direction and removed easily from the handpiece (85). In this manner, the dental professional can remove the prophy angle after treating a patient, dispose of it, sterilize the handpiece, and place a new prophy angle onto the handpiece.

Workers skilled in the art will appreciate that various modifications can be made to the illustrated embodiments and description herein without departing from the spirit and scope of the present invention. For example, the protruding locking annular member (94) of the handpiece (85) (as shown in FIGS. 2-9D) could be modified so that it is a recessed groove. Conversely, the grooves (undercut areas) adjacent to the locking tabs (55, 57) (as shown in FIGS. 2-9D) on the prophy angle (40) could be modified so that they are protruding rings. It is also recognized that the locking member in the handpiece could have a different structure than the protruding annular locking member (94) shown in FIGS. 2-9D. For example, ball detents or dimples could be used as the locking member in the handpiece (85).

The foregoing are only some examples of modifications that can be made to the illustrated embodiments and description herein without departing from the spirit and scope of the present invention. It is intended that all such modifications within the spirit and scope of the present invention be covered by the appended claims.

What is claimed is:

1. A dental handpiece and prophy angle assembly, comprising:
   (i) a disposable dental prophy angle having an elongated tubular body with proximal and distal end portions, the tubular body containing a central bore extending therethrough, the proximal end portion including a hollow head member for mounting a driven gear therein, the distal end including a first locking extension with first locking tab and a second locking extension with second locking tab, the distal end being open-ended so that the prophy angle can be removably attached to a dental handpiece, and the central bore including a drive shaft having forward-facing and rear-facing end portions, the forward-facing end of the drive shaft including a driving gear for driving the driven gear and the rear-facing end of the drive shaft having a piloting tip for guiding the prophy angle onto the handpiece, the drive shaft further having first and second protruding self-aligning tabs to form a recessed locking surface located there between for receiving an interlocking drive member located in the handpiece; and
   (ii) the dental handpiece comprising a forward-facing tubular nose portion and a rear-facing handle portion, the nose portion including a central aperture therein for removably receiving the piloting tip of the drive shaft and a locking annular member for engaging the first and second locking tabs to lock the prophy angle in place, and the handpiece including an interlocking drive member, the drive member having first and second self-aligning forward-facing extension prongs to form a locking slot located there between so that the extension prongs may slide into the recessed locking surface of the drive shaft.

2. The dental handpiece and prophy angle assembly of claim 1, wherein the axis of the driven gear of the prophy angle is angled at 90 degrees with respect to the axis of the driving gear of the prophy angle.

3. The dental handpiece and prophy angle assembly of claim 1, wherein the axis of the driven gear of the prophy angle is angled at an angle in the range of about 90 to about 130 degrees with respect to the axis of the driving gear of the prophy angle.

4. The dental handpiece and prophy angle assembly of claim 1, wherein the axis of the driven gear of the prophy angle is angled at an angle of 108 degrees with respect to the axis of the driving gear of the prophy angle.

5. The dental handpiece and prophy angle assembly of claim 1, wherein the driven gear and driving gear of the prophy angle each include beveled gear teeth such that the gear teeth of the driven gear and the gear teeth of the driving gear can intermesh together.

6. The dental handpiece and prophy angle assembly of claim 5, wherein the gear teeth of the driven gear and driving gear are staggered in relation to each other.

7. The dental handpiece and prophy angle assembly of claim 1, wherein the head member of the prophy angle includes a hinged closure.

8. The dental handpiece and prophy angle assembly of claim 7, wherein the hinged closure is secured to the prophy angle by locking detents on the head member that snap into slots in the hinged closure.

9. The dental handpiece and prophy angle assembly of claim 7, wherein the prophy angle includes a handle portion at its distal end, the handle portion having a textured external surface.

10. The dental handpiece and prophy angle assembly of claim 1, wherein a prophylaxis cup is supported by the driven gear of the prophy angle.

11. The dental handpiece and prophy angle assembly of claim 1, wherein a prophylaxis brush cup is supported by the driven gear of the prophy angle.

12. The dental handpiece and prophy angle assembly of claim 1, wherein the nose portion of the dental handpiece further includes nesting surfaces and the locking extensions located on the distal end of the prophy angle mate with the nesting surfaces.

13. The dental handpiece and prophy angle assembly of claim 1, wherein the distal end of the prophy angle further includes locking recessions and the nose portion of the dental handpiece further includes nesting surfaces, the locking recessions and nesting surfaces being complementary-shaped so that the locking recessions of the prophy angle mate with the nesting surfaces of the dental handpiece.

14. A disposable dental prophy angle, comprising:
(i) an elongated tubular body with proximal and distal end portions, the tubular body containing a central bore extending therethrough, the proximal end portion including a hollow head member for mounting a driven gear therein, the distal end including a first locking extension with first locking tab and a second locking extension with second locking tab, the distal end being open-ended so that the prophy angle can be removably attached to a dental handpiece; and
(ii) a drive shaft positioned within the central bore, the drive shaft having forward-facing and rear-facing end portions, the forward-facing end of the drive shaft including a driving gear for driving the driven gear and the rear-facing end of the drive shaft having a piloting tip for guiding the prophy angle onto the handpiece, the drive shaft further having first and second protruding self-aligning tabs to form a recessed locking surface located there between for receiving an interlocking drive member located in the handpiece.

15. The dental prophy angle of claim 14, wherein the axis of the driven gear of the prophy angle is angled at 90 degrees with respect to the axis of the driving gear of the prophy angle.

16. The dental prophy angle of claim 14, wherein the axis of the driven gear of the prophy angle is angled at an angle in the range of about 90 to about 130 degrees with respect to the axis of the driving gear of the prophy angle.

17. The dental prophy angle assembly of claim 14, wherein the axis of the driven gear of the prophy angle is angled at an angle of 108 degrees with respect to the axis of the driving gear of the prophy angle.

18. The dental handpiece and prophy angle assembly of claim 14, wherein the driven gear and driving gear of the prophy angle each include beveled gear teeth such that the gear teeth of the driven gear and the gear teeth of the driving gear can intermesh together.

19. The dental handpiece and prophy angle assembly of claim 18, wherein the gear teeth of the driven gear and driving gear are staggered in relation to each other.

20. The dental prophy angle of claim 14, wherein the head member of the prophy angle includes a hinged closure.

21. The dental prophy angle of claim 20, wherein the hinged closure is secured to the prophy angle by locking detents on the head member that snap into slots in the hinged closure.

22. The dental prophy angle of claim 14, wherein the prophy angle includes a handle portion at its distal end, the handle portion having a textured external surface.

23. The dental prophy angle of claim 14, wherein a prophylaxis cup is supported by the driven gear of the prophy angle.

24. The dental prophy angle of claim 14, wherein a prophylaxis brush cup is supported by the driven gear of the prophy angle.

25. The dental handpiece and prophy angle assembly of claim 1, wherein the recessed locking surface extends along a substantially same axis as the central bore and the locking slot has a substantially same axis as the axis of the recessed locking surface.

26. The dental prophy angle of claim 14, wherein the recessed locking surface extends along a substantially same axis as the central bore and the interlocking drive member is located along a substantially same axis as the axis of the recessed locking surface.

27. The dental handpiece and prophy angle assembly of claim 1, wherein the distal end of the prophy angle comprises more than two locking extensions with locking tabs.

28. The dental prophy angle of claim 14, wherein the distal end of the prophy angle comprises more than two locking extensions with locking tabs.

* * * * *